United States Patent
Van Gool et al.

(10) Patent No.: US 12,370,287 B2
(45) Date of Patent: Jul. 29, 2025

(54) PARTICULATE GEL FOR THE TREATMENT OF A BLEEDING IN THE SINUS OR NASAL CAVITY

(71) Applicant: BIOMED ELEMENTS B.V., Nijmegen (NL)

(72) Inventors: Jasper Johannes Franciscus Van Gool, Grave (NL); Daniel Laurentiu Jongen, Wageningen (NL); Antonius Andreas Maria Voermans, Nijmegen (NL); Martinus Gerardus Eimbertus Van De Goor, Nijmegen (NL)

(73) Assignee: BIOMED ELEMENTS B.V., Nijmegen (NL)

( * ) Notice: Subject to any disclaimer, the term of this patent is extended or adjusted under 35 U.S.C. 154(b) by 745 days.

(21) Appl. No.: 17/436,759

(22) PCT Filed: Mar. 8, 2020

(86) PCT No.: PCT/NL2020/050153
§ 371 (c)(1),
(2) Date: Sep. 7, 2021

(87) PCT Pub. No.: WO2020/185074
PCT Pub. Date: Sep. 17, 2020

(65) Prior Publication Data
US 2022/0184273 A1 Jun. 16, 2022

(30) Foreign Application Priority Data
Mar. 8, 2019 (NL) .................... 2022695

(51) Int. Cl.
| | | |
|---|---|---|
| *A61L 26/00* | (2006.01) | |
| *C08J 3/00* | (2006.01) | |
| *C08J 3/075* | (2006.01) | |
| *C08J 3/12* | (2006.01) | |
| *C08J 3/24* | (2006.01) | |
| *C08J 9/28* | (2006.01) | |
| *C08L 89/06* | (2006.01) | |

(52) U.S. Cl.
CPC ....... *A61L 26/0038* (2013.01); *A61L 26/0023* (2013.01); *A61L 26/0052* (2013.01); *A61L 26/008* (2013.01); *A61L 26/0085* (2013.01); *C08J 3/005* (2013.01); *C08J 3/075* (2013.01); *C08J 3/122* (2013.01); *C08J 3/24* (2013.01); *C08J 9/283* (2013.01); *C08J 2207/10* (2013.01); *C08J 2389/04* (2013.01); *C08J 2401/28* (2013.01); *C08J 2405/00* (2013.01); *C08J 2489/04* (2013.01)

(58) Field of Classification Search
CPC ............ A61L 2400/04; A61L 26/0023; A61L 26/0038; A61L 26/0052; A61L 26/0085; C08J 2207/10; C08J 2389/04; C08J 2401/28; C08J 2405/00; C08J 2489/04; C08J 3/005; C08J 3/075; C08J 3/122; C08J 3/24; C08J 9/283
See application file for complete search history.

(56) References Cited

U.S. PATENT DOCUMENTS

| | | | |
|---|---|---|---|
| 2003/0009145 A1* | 1/2003 | Struijker-Boudier | A61P 9/00 604/500 |
| 2013/0096082 A1 | 4/2013 | Harkamp et al. | |

FOREIGN PATENT DOCUMENTS

| | | |
|---|---|---|
| EP | 3934704 | 9/2022 |
| WO | 00/76533 | 12/2000 |
| WO | 2010/132028 | 11/2010 |
| WO | 2013/060770 | 5/2013 |

OTHER PUBLICATIONS

DreXIer et al., "Dehydrothermal Crosslinking of Electrospun Collagen," Tissue Engineering, Part C, 2011, 17(1): 9-17. (Year: 2011).*
International Search Report for PCT/NL2020/050153, mailed May 15, 2020, 4 pages.
Written Opinion of the ISA for PCT/NL2020/050153, mailed May 15, 2020, 7 pages.

* cited by examiner

*Primary Examiner* — Julie Ha
(74) *Attorney, Agent, or Firm* — NIXON & VANDERHYE P.C.

(57) ABSTRACT

Gels which include a first gelatin component and a second gelatin component in an aqueous medium are described, wherein the first gelatin component includes gelatin particles having chemical cross-links and dehydrothermal cross-links, and the second gelatin component includes a dissolved gelatin having chemical cross-links and at least one polysaccharide.

15 Claims, 1 Drawing Sheet

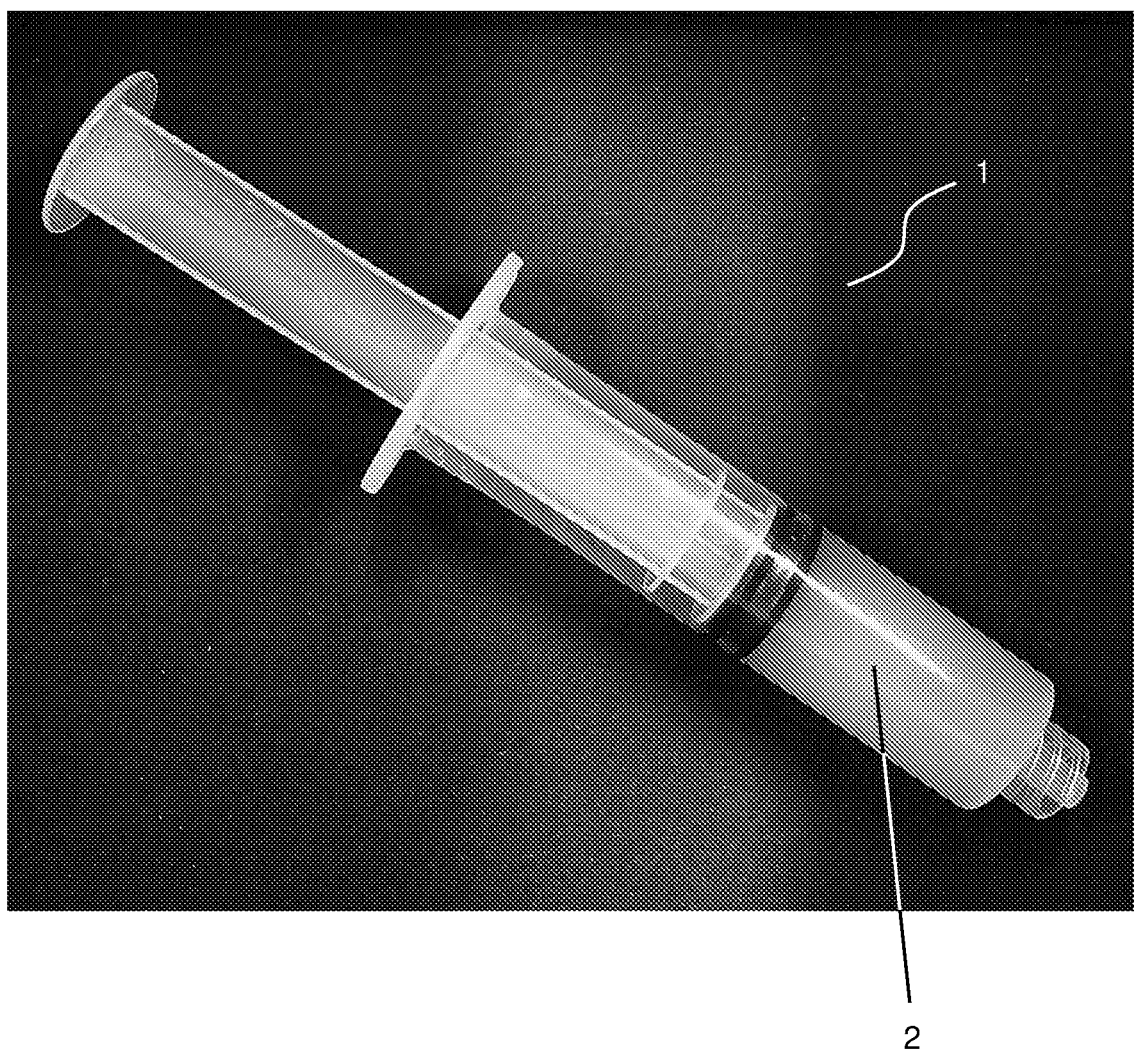

PARTICULATE GEL FOR THE TREATMENT OF A BLEEDING IN THE SINUS OR NASAL CAVITY

This application is the U.S. national phase of International Application No. PCT/NL2020/050153 filed 8 Mar. 2020, which designated the U.S. and claims priority to NL Patent Application No. 2022695 filed 8 Mar. 2019, the entire contents of each of which are hereby incorporated by reference.

The invention relates to a gel, to a method of preparing the gel and to a gel for use in the treatment of a bleeding site, in particular a bleeding site in the sinus cavity or nasal cavity.

Haemostasis at a wound or bleeding site can nowadays effectively be achieved by dressings that not only prevent the direct blood loss, but also actively induce the coagulation of blood—a natural process that often needs assistance in case of severe bleeding. Such dressings often comprise a (hydro) gel that is based on gelatin. The spongy physical properties of such gel hasten clot formation and provide structural support for the forming clot.

Gelatin dressings are usually prepared by foaming a solution of gelatin, followed by drying the resulting foam (e.g. by lyophilization). Since gelatin is generally soluble at physiological temperature, the preparation of a gelatin dressing usually involves the cross-linking of the gelatin. Particles of cross-linked gelatin in an aqueous medium then form a particulate gelatin gel. This prevents instantaneous dissolution of the gelatin at a bleeding site and provides a network structure in combination with spongy physical properties. Methods of cross-linking may comprise treatment of the dissolved gelatin with a chemical cross-linking agent or treatment of the dry (e.g. lyophilized) gelatin with dry heat (e.g. at a temperature of 100-190° C. for several hours).

It is contemplated that the action of gelatin is linked to its ability to absorb and hold blood and other fluids, in amounts of many times its own weight. Moreover, it is thought that caught blood platelets interact with the gelatin and initiate the coagulation cascade that naturally occurs in the body after injury.

When current particulate gelatin gels are used to stop a bleeding, the particles break up and the gel bursts when excessive amounts of fluid are absorbed. This results in loss of network structure of the gel and in dissipation of the gel from the bleeding site. Although the presence of gelatin at a wound is by definition of a transient nature, such dissipation often occurs prematurely, e.g. before sufficient wound healing has occurred. Especially when the gelatin is used in body cavities, the premature disruption of gelatin is a problem because of the fluids, the moist and the high humidity in such places. For example, for the treatment of epistaxis (nose bleeding), there is at present no satisfactory gelatin-comprising composition (such as a particulate gel) that remains stable after insertion into the nasal cavity during the time that is required for the healing of the bleeding site. More generally, at present there is no method available that allows the tuning of the stability of gelatin so that gelatins can be designed in a targeted manner that have predetermined times after which substantial degradation and loss of their structural integrity take place.

It is therefore an objective of the present invention to provide a gelatin composition that remains structurally stable for a longer period of time than known gelatin compositions do, in particular that the gelatin composition is capable of achieving haemostasis in a body cavity before it liquefies and dissipates from the cavity. More generally, it is an object to manufacture a gelatin of which the degradation can be tuned given the conditions in which it is applied.

It has now been found that one or more of these objectives can be reached by applying particular preparation method of the gelatin.

Accordingly, the present invention relates to a gel comprising a first gelatin component and a second gelatin component in an aqueous medium, wherein the first gelatin component comprises gelatin particles comprising chemical cross-links and dehydrothermal cross-links;

the second gelatin component comprises a dissolved gelatin comprising chemical cross-links and at least one polysaccharide, in particular a glycosaminoglycan.

FIG. 1 displays a syringe that is filled with a gel according to the invention.

Gelatin is a mixture of peptides and proteins that is obtained by partial hydrolysis of collagen extracted from animal tissues such as skin, bones, and connective tissues. Its chemical composition is in many aspects closely similar to that of its parent collagen. Gelatin readily dissolves in hot water and sets to a gel on cooling. However, it usually does not dissolve well when added to cold water.

A gel of the invention comprises two different types of gelatin, which for the purpose of the invention have been assigned the names "first gelatin component" and "second gelatin component". The gelatins of the first component and the second component may in principle be any gelatin. For example, the gelatins are independently of each other derived from a species selected from the group of pig, cow, horse, goat, sheep, fish and various poultry species. Preferably, however, it is selected from the group of pig, cow and horse. For application at body temperature, these gelatins are particularly suitable in view of their melting points.

Both components are present in a liquid aqueous medium. Such medium typically comprises at least 50 wt. % of water and less than 50 wt. % of one or more other liquids. The medium may also comprise at least 75 wt. % of water, at least 85 wt. % of water, at least 90 wt. % of water, at least 95 wt. % of water, at least 98 wt. % of water or at least 99 wt. % of water. The medium may also consist of water (i.e. it contains 100 wt. % of water).

The first gelatin component comprises gelatin particles. These particles are formed from cross-linked gelatin, wherein the gelatin comprises chemical cross-links as well as dehydrothermal cross-links. With the presence of both types of cross-links, the gelatin particles obtain the required structural properties for forming the gel of the invention.

Chemical cross-links are formed by reaction of the gelatin with chemical cross-linking agents. For example, such cross-linking agents are mono-aldehydes such as formaldehyde or di-aldehydes such as glutaraldehyde. The cross-links that result from these cross-linking agents are commonly said to be derived from the respective cross-linking agent. Accordingly, in a gel of the invention, the chemical cross-links of the gelatin particles and/or the dissolved gelatin may independently of each other be derived from an aldehyde, in particular a dialdehyde. For example, the chemical cross-links are derived from an aldehyde selected from the group of formaldehyde, paraformaldehyde, acetaldehyde, propionaldehyde, PEG-propiondialdehyde, butyraldehyde, isobutyraldehyde, valeraldehyde, heptaldehyde, decanal, terephthaldehyde, crotonaldehyde, glutaraldehyde, glyoxal, PEG-dialdehyde, dialdehyde carboxymethyl cellulose (DCMC) and dialdehyde starch (DAS).

Dehydrothermal cross-links are formed when the gelatin is exposed to an elevated temperature at which water is released. For example, a terminal amine group of e.g. a lysine moiety in the gelatin may react with an aldehyde group of another moiety in the gelatin under the release of water.

The solid gelatin with the chemical and dehydrothermal cross-links is present as small particles, obtained by lyophilizing a foam of the cross-linked gelatin, followed by pulverizing the lyophilizate. These particles usually have at least one dimension in the range of 10-1000 μm or in the range of 50-750 μm. In particular, at least one dimension is in the range of 75-500 μm, more in particular in the range of 75-250 μm. The aspect ratio of a particle in a gel of the invention is usually in the range of 1-5, preferably in the range of 1-3. In this respect, the aspect ratio of a particle is defined as the ratio of the longest dimension to the shortest dimension of the particle.

Usually, the ranges given for the dimensions of the particles are ranges that apply to at least 95% of the particles (i.e. at least 95% of the particles fall within a given range). For example, at least 95% of the particles has at least one dimension in the range of 75-500 μm, in particular at least 95% of the particles has at least one dimension in the range of 75-250 μm. Such distribution is measured with e.g. Dynamic Image Analysis (DIA), making use of a Camsizer P4 particle analyzer (Retsch Technology).

The second gelatin component also comprises cross-linked gelatin. However, this gelatin has not been subjected to dehydrothermal cross-linking and therefore does not comprise dehydrothermal cross-links. It has been chemically cross-linked to such extent that it is sufficiently soluble in water. Usually, this cross-linked gelatin does not form a gel with water. Accordingly, the gelatin of the second gelatin component is dissolved in a gel of the invention. The particles of the first gelatin component are suspended in this gel. A gel of the invention is therefore termed a "particulate gel".

The polysaccharide in a gel of the invention is usually dissolved and may be selected from the group of polysaccharide derived from bacteria, polysaccharide derived from fungi, polysaccharide derived from plants and polysaccharide derived from animals. For example, the polysaccharide is selected from the group of xanthan, dextran, gellan, levan, curdlan, cellulose (including cellulose derivatives), carboxymethylcellulose, hemicellulose, pullulan, starch, agar, agarose, alginate, carrageenan, pectin, konjac, gums (such as beta-mannan gum, carob gum, fenugreek gum, guar gum, tara gum, karaya gum, tragacanth gum, arabinoxylan gum, gellan gum, xanthan gum), chitosan (including chitosan derivatives) and hyaluronic acid (including hyaluronic acid derivatives). The gelatin may be covalently bound to the polysaccharide, but this is not necessary.

Preferably, the polysaccharide is a glycosaminoglycan, which is an unbranched polysaccharide comprising a repeating disaccharide unit. A glycosaminoglycan is in particular selected from the group of heparin, heparan sulfate, chondroitin sulfate, dermatan sulfate, keratan sulfate and hyaluronic acid. The glycosaminoglycan may be present as a glycosaminoglycan derivative, for example a derivative wherein an additional moiety is connected to the glycosaminoglycan by means of e.g. an amide of ester connection.

The gelatin may be covalently bound to the polysaccharide, e.g. by chemical cross-linking. For example, when the polysaccharide is a glycosaminoglycan (such as hyaluronic acid), it may be covalently bound to the polysaccharide.

The mass average molecular mass ($M_w$) of the polysaccharide is usually at least 10 kDa. Typically, it is in the range of 100-10,000 kDa or in the range of 200-5,000 kDa. In case the polysaccharide is a glycosaminoglycan, then the molecular mass ($M_w$) is usually in the range of 100-10,000 kDa, more preferably it is in the range of 200-5,000 kDa or in the range of 300-3,000 kDa.

A gel of the invention may comprise a pH buffer solution, for example a phosphate buffered saline (PBS). Another suitable buffer solution is Ringer's solution (typically comprising sodium chloride, potassium chloride, calcium chloride and sodium bicarbonate), or Tyrode's solution (typically comprising sodium chloride, potassium chloride, calcium chloride, magnesium chloride, sodium dihydrogen phosphate and sodium bicarbonate).

The pH of a gel of the invention is usually in the range of 6.4 to 7.8, in particular in the range of 6.8 to 7.4. Such pH may be reached by applying a buffer having an appropriate pH, or by setting the pH at a desired value by using appropriate amounts of acid and/or base in an aqueous medium, such as demineralized water.

A gel of the invention may have undergone a sterilization process to provide the gel as a sterile gel. For example, the gel is sterilized by exposure to high temperature (e.g. by steam sterilization) or to high energy radiation (e.g. gamma radiation).

The viscosity of a gel of the invention may be tuned by varying certain characteristics of the gel such as the amount and size of the particles, the degree of cross-linking of the gelatin(s) used, and the relative abundancy of the first gelatin component and the second gelatin component. Depending on the application of the gel, a higher or a lower viscosity can be set. For example, for topical administration on the skin, the gel should not dissipate from the site of administration. Also, for application in the nasal cavity it is required that the gel does not seep out of the cavity.

The dynamic viscosity of a gel of the invention is usually in the range of 5-250 Pa·s. It may also be in the range of 5-200 Pa·s, in the range of 5-100 Pa·s or in the range of 5-40 Pa·s. In particular, it is in the range of 10-30 Pa·s, more in particular in the range of 10-25 Pa·s or 15-30 Pa·s. Even more in particular, it is in the range of 15-25 Pa·s. A person skilled in the art will be able to find the conditions that are required for reaching a certain viscosity by routine experimentation and without exerting an inventive effort.

It is an advantage of the gel of the invention that the gel is capable of absorbing large quantities of fluid (such as blood and water) without disintegration of the gel, as is e.g. demonstrated by the water absorption experiments in the Examples. Whereas in conventional particulate gels the particles are prone to bursting when excessive amounts of fluid are absorbed, the particles in a gel of the invention are resistant to this. This makes that it is advantageous to use a gel of the invention for the treatment of a bleeding. At the same time, the gel quickly realizes a barrier by forming a clot at the bleeding site, so that the bleeding stops.

A further advantageous effect of a gel of the invention is that the actual healing of the site of bleeding is faster than with known gels.

A gel of the invention is particularly advantageous when applied in the nasal cavity to treat a bleeding in the nasal cavity and sinus cavity, because the gel maintains its network structure and remains in place, i.e. it does not dissipate from the bleeding site, despite the high humidity in the nasal cavity and sinus cavity. This property is e.g. supported by both the water occlusion and the dynamic viscosity measurements in the Examples. Further, it appeared that the actual healing of the site of a bleeding in the nasal or sinus cavity is also faster than with known gels.

A problem that is often encountered with the application of haemostatic material in the nasal cavity and sinus cavity, is that the shape of the walls in the cavities is not well-adopted by the material, so that the gel prematurely releases from the cavity and the bleeding cannot be sufficiently stopped. A gel of the invention provides a solution to this problem because upon application the gel forms a barrier in the nasal or sinus cavity that easily and accurately adopts the desired shape, i.e. the complementary shape of the cavity wall. At the same time, the gel of the invention has an improved occlusion in the cavity in that it stays well in place for a longer time, as is e.g. demonstrated by the water occlusion experiments in the Examples. Moreover, the barrier is easy to remove once the wound has healed.

The invention further relates to a method for preparing a gel as described hereinabove, comprising
preparing a first gelatin component by performing the steps of
providing an aqueous composition comprising dissolved gelatin; then
cross-linking the gelatin in the composition by treating the gelatin with a chemical cross-linking agent; then
foaming of the aqueous composition to yield a foam; then
lyophilizing the foam to yield a porous solid; then
pulverizing the porous solid to yield a powder; then
exposing the powder to dehydrothermal curing; then
remoisturizing the powder to yield the first gelatin component;
preparing a second gelatin component by performing the steps of
providing an aqueous composition comprising dissolved gelatin; then
cross-linking the gelatin in the composition by treating the gelatin with a chemical cross-linking agent; and
adding a polysaccharide to the composition before or after the cross-linking with a chemical cross-linking agent;
mixing the first gelatin component with the second gelatin component to yield the gel.

In the method of the invention, the first gelatin component and the second gelatin component are prepared separately, after which they are mixed to form the gel of the invention.

The gelatin starting material for any of the two components may, independently of each other, be derived from a species selected from the group of pig, cow, horse, goat, sheep, fish and various poultry species. Preferably, however, it is selected from the group of pig, cow and horse.

The cross-linking of the gelatin in the preparation of the first gelatin component and the second gelatin component is usually performed with an aldehyde, in particular an aldehyde selected from the group of formaldehyde, paraformaldehyde, acetaldehyde, propionaldehyde, PEG-propiondialdehyde, butyraldehyde, isobutyraldehyde, valeraldehyde, heptaldehyde, decanal, terephthaldehyde, crotonaldehyde, glutaraldehyde, glyoxal, PEG-dialdehyde, dialdehyde carboxymethyl cellulose (DCMC) and dialdehyde starch (DAS). The aldehydes in each preparation can be chosen independently of each other.

In the preparation of the first component, an aqueous composition comprising the chemically cross-linked gelatin is foamed to yield a gelatin foam with a density that is usually in the range of 1.5-12 mL/g, in particular in the range of 1.5-9 mL/g. Preferably, it is in the range of 2.0-6.0 mL/g. Lyophilization of the foam typically yields a dry and porous cake, which is then pulverized into particles having at least one dimension of preferably less than 1.0 mm. Pulverization may be performed by first cutting the cake into shapes having all dimensions in the range of e.g. 2-10 mm, followed by grinding the shapes in a grinding machine to yield particles with smaller dimension. For example, these particles usually have at least one dimension in the range of 10-1000 µm or in the range of 50-750 µm. In particular, at least one dimension is in the range of 75-500 µm, more in particular in the range of 75-250 µm. The aspect ratio of a particle that is formed in a method of the invention is usually in the range of 1-5, preferably in the range of 1-3. In this respect, the aspect ratio of a particle is defined as the ratio of the longest dimension to the shortest dimension of the particle.

If the size distribution of the particles thus formed needs an adjustment, a sieve may be used. For example, particles with dimensions in a desired range may be obtained by sieving the particles of the grinded cake over sieves with the corresponding mesh. For example, the dimensions of the particles in the powder after appropriate sieving are in the range of 50-750 µm, preferably in the range of 75-500 µm.

In the preparation of the second component, the polysaccharide is typically added after the cross-linking of the gelatin. It may however also be added before the cross-linking.

It is in principle also possible to prepare a second component that lacks the polysaccharide, and add the polysaccharide only after both gelatin components have been mixed. Accordingly, the present invention further relates to a method for preparing a gel as described hereinabove, comprising
preparing a first gelatin component by performing the steps of
providing an aqueous composition comprising dissolved gelatin; then
cross-linking the gelatin in the composition by treating the gelatin with a chemical cross-linking agent; then
foaming of the aqueous composition to yield a foam; then
lyophilizing the foam to yield a porous solid; then
pulverizing the porous solid to yield a powder; then
exposing the powder to dehydrothermal curing; then
remoisturizing the powder to yield the first gelatin component;
preparing a second gelatin component by performing the steps of
providing an aqueous composition comprising dissolved gelatin; then
cross-linking the gelatin in the composition by treating the gelatin with a chemical cross-linking agent;
mixing the first gelatin component with the second gelatin component to yield the gel; then
adding a polysaccharide to the composition before or after the cross-linking with a chemical cross-linking agent.

A method of the invention may include a sterilization step, yielding the gel of the invention as a sterile gel. For example, a gel that has been formed after the mixing of both gelatin components may be exposed to an elevated temperature, e.g. to a temperature in the range of 80-140° C., in particular in the range of 100-135° C. The temperature and the period of exposure are then chosen such that any micro-organisms are destroyed to a desired extent, whilst not degrading the gel too much. For example, the gel is exposed during 15-20 minutes (e.g. at a temperature in the range of 115-125° C.), or it is exposed during 2-10 minutes (e.g. at a temperature in the range of 130-140° C.). Surprisingly, there appears to be an optimum in the temperature and duration of the heat exposure wherein the properties of the gel first improve, while after a certain period the gel starts to deteriorate (i.e. it liquefies and so detaches from the bleeding site).

Sterilization may also be achieved by exposing the gel to high energy radiation, in particular ionizing radiation such as gamma rays, X-rays, and the higher ultraviolet part of the electromagnetic spectrum. The dosage to which a gel may be exposed is e.g. 15, 25 or 50 kGy.

In the event that the polysaccharide is added only after the mixing of both gelatin components, the addition needs to precede a sterilization step, if such step is performed.

The invention further relates to a gel obtainable by the method as described hereinabove.

An important use of a gel of the invention is in the medical field. Accordingly, the invention further relates to a gel as described hereinabove, for use in medical therapy, for use as a medicament and/or for use in medicine.

The invention further relates to a gel as described hereinabove, for use in the treatment of a bleeding site, in particular a bleeding site in the nasal cavity or sinus cavity. In a preferred embodiment, a gel according to the invention is provided for use in the treatment of epistaxis. This may be a gel wherein 3-15 grams of the gel are applied to the bleeding site, in particular 5-10 g.

The invention further relates to a method, or a gel according to the invention for use in a method of treating a bleeding site of a human or an animal, the method comprising administering to the bleeding site an amount of a gel as described hereinabove effective to stop bleeding at the bleeding site. Such bleeding site is preferably the nasal cavity or sinus cavity in a human or an animal. By the phrase "administering the gel to the bleeding site" is meant that the gel is applied to the bleeding site so that the bleeding site is in touch with the gel. The effect of such treatment is that the bleeding stops and the wound heals. An effective amount of the gel to stop bleeding at the bleeding site of a human or an animal is usually in the range of 3-15 mL. In particular it is in the range of 3-9 mL, in the range of 6-12 mL or in the range of 9-15 mL, depending on the size of the cavity.

The gel may be provided in any suitable form, for example in a syringe for ease of application to e.g. the nasal cavity. Accordingly, the invention further relates to a syringe comprising an effective amount of the gel in order to stop bleeding at a bleeding site of a human or animal subject. FIG. 1 displays a syringe (1) that is filled with a gel (2) of the invention. This syringe is suitable for applying a gel of the invention to a human or animal. In a preferred embodiment, the gel is sterilized after or before filling the syringe (or other packaging means) with the gel, to e.g. to increase shelf-life of the gel.

The invention further relates to the use of a gel as described hereinabove for treating a bleeding site of a human or an animal, in particular a bleeding of the sinus or nasal cavity, such as an epistaxis. The gel may also be used for the promotion of hemostasis in an individual in need thereof.

The invention further relates to the use of a gel as described hereinabove for the manufacture of a medicament for treating a bleeding site of a human or an animal, in particular a bleeding of the sinus or nasal cavity, such as an epistaxis. The gel may also be used for the promotion of hemostasis in an individual in need thereof.

EXAMPLES

Example 1: Preparation of Porous Gelatin Particles

In a large glass bottle, 75.00 g of gelatin (Pig skin, Type A, 285 bloom) were added to 1,175 g of demineralized water of 45° C., after which the gelatin was left to dissolve. Once fully dissolved, the solution was cooled to 35° C. After about one hour, 1.013 mL of a 37 wt. % formaldehyde solution in water was added. The gelatin was then left to cross-link for 3 hours.

A gelatin foam was created using a Kenwood Chef premier mixer. The mixing bucket was charged with 1,250 g of the aqueous cross-linked gelatin solution as prepared above. After connecting the mixing bucket to the mixer, the gelatin solution was whisked during 30 minutes using speed setting 6, yielding a foam with a density of 2.91 mL/g.

Three lyophilization plates were filled with 330-340 g of the foam as prepared above and loaded into a standard, plate based, freeze dryer that was pre-cooled to −40° C. After freezing for 3 hours, the lyophilization cycle was started. The material was then lyophilized during 64 hours yielding three dried gelatin sponges.

The dried gelatin sponges as prepared above were milled using a Retsch ZM 200 ultra centrifugal mill. The sponges were first pre-cut to roughly 0.5×0.5×1.0 cm and thereafter added to the mill in a continuous flow over the course of 5 minutes. The milling occurred at 18,000 rpm. In the first milling cycle, a 1.00 mm sieve was installed in the mill. The particles that passed this sieve were then subjected to a second cycle using a sieve of 0.50 mm. The particles that passed this sieve were then subjected to a third cycle using a sieve of 0.25 mm. The particles that passed this last sieve formed a white powder of porous gelatin particles.

The porous gelatin particles as prepared above were exposed to a dehydrothermal curing step. First, paper bags of 9×5×16.8 cm were each filled with 9.00 g of gelatin particles. The filled paper bags were placed up-right in an oven rack of a Binder forced convection oven that was pre-heated to 140° C. The porous gelatin particles were then cured during 6 hours at this temperature. After the curing, the porous gelatin particles were left to remoisturize in ambient air, after which they were ready for use in the preparation of the gels of the invention.

Example 2: Reference Gel

In a small plastic container, 1.00 g of the porous gelatin particles obtained according to the procedure of Example 1 was mixed with 9.00 g of phosphate buffered saline (pH 7.4). The resulting mixture was left to equilibrate for 6 hours. The obtained gel was mixed again before transferring it into a syringe. The filled syringe was steam sterilized using a standard steam sterilization cycle operating at 121° C. for 20 minutes.

Example 3: Gel of the Invention with Carboxymethyl Cellulose

A 2.0 wt. % carboxymethyl cellulose solution was prepared as follows. An amount of 0.20 g of carboxymethyl cellulose (700 kDa, degree of substitution 0.9) was mixed with 9.80 g of phosphate buffered saline (pH 7.4) in a small glass container. The mixture was then stirred for 2 hours to dissolve the carboxymethyl cellulose.

A 3.0 wt. % gelatin solution was prepared as follows. An amount of 0.754 g of gelatin (Pig skin, Type A, 285 bloom) was mixed with 24.25 g of phosphate buffered saline (pH 7.4) in a small glass container at 45° C. Once dissolved, 10 µL of a 37 wt. % formaldehyde solution in water was added. The gelatin solution was then left to cross-link for 18 hours.

In a small plastic container, 2.00 g of the 2.0 wt. % carboxymethyl cellulose solution were mixed with 6.00 g of the 3.0 wt. % cross-linked gelatin solution with the aid of a spatula. Then, 0.798 g of the porous gelatin particles of Example 1 were added to the plastic container and mixed with the solution. The resulting mixture was left to equilibrate for 6 hours. The created gel was transferred into a syringe and steam sterilized as described in Example 2.

Example 4: Gel of the Invention with Chitosan

A 2.0 wt. % chitosan solution was prepared as follows. An amount of 0.53 g of chitosan was mixed with 26.48 g of a 2.0 wt. % acetic acid solution in water in a small glass container. The mixture was then stirred for 1 hour to dissolve the chitosan.

A 1.5 wt. % gelatin solution was prepared as follows. An amount of 0.291 g of gelatin (Pig skin, Type A, 285 bloom) was mixed with 19.13 g of phosphate buffered saline (pH 7.4) in a small glass container at 45° C.

The dissolved chitosan and the dissolved gelatin were then mixed with each other in a 1 to 1 ratio. In a small plastic container, 19.0 g of the 2.0 wt. % chitosan solution were mixed with 19.0 g of the 1.5 wt. % gelatin solution. Under stirring, the resulting solution was warmed to 35° C., after which 10 µL of a 37 wt. % formaldehyde solution in water were added. It was then left to cross-link for 3 hours.

Then, 6.05 g of the chitosan/gelatin solution was mixed with 0.605 g of the porous gelatin particles of Example 1 in a plastic container. The resulting mixture was left to equilibrate for 6 hours. The created gel was transferred into a syringe and steam sterilized as described in Example 2.

Example 5: Gel of the Invention with Guar Gum

A 2.66 wt. % guar gum solution was prepared as follows. An amount of 0.27 g of guar gum was mixed with 9.83 g of phosphate buffered saline in a small glass container. The mixture was then stirred for 40 hours to dissolve the guar gum.

A 3.0 wt. % gelatin solution was prepared according to the procedure as described in Example 3, with the difference that the gelatin solution was left to cross-link for 2 hours instead of 18 hours.

In a small plastic container, 10.0 g of the 2.66 wt. % guar gum solution were mixed with 3.35 g of the 3.0 wt. % cross-linked gelatin solution during stirring for 2 hours. Then, 0.626 g of the porous gelatin particles of Example 1 were added to the plastic container and mixed with the solution. The resulting mixture was left to equilibrate for 6 hours. The created gel was transferred into a syringe and steam sterilized as described in Example 2.

Then, 6.364 g of the guar gum/gelatin solution was mixed with 0.626 g of the porous gelatin particles of Example 1 in a plastic container. The resulting mixture was left to equilibrate for 6 hours. The created gel was transferred into a syringe and steam sterilized as described in Example 2.

Water Absorption Test Method

The water absorption capacity of the prepared gels was analyzed using the following standardized absorption method.

An amount of 1.00 g of gel was weighted into a container and a 4-fold excess of demineralized water was added. The container was closed off and the gel was mixed with the demineralized water by vortexing the container for 15 seconds. The gel was then left to absorb the water for 2 hours.

Excess demineralized water was removed as the supernatant resulting from centrifugation using an Eppendorf (5810) centrifuge at 4,000 rpm for 15 minutes followed by letting the container stand during 15 minutes. The total amount of water absorbed was determined by subtracting the amount of removed water from the initial amount of excess water that was added. The total water absorption of the gel was calculated as the percentage of the initial starting weight of the tested gel.

Occlusion Test Method

The sealing/barrier formation capabilities of the prepared gels were assessed with the following standardized occlusion test.

A glass test tube of 7 mL having an inner diameter of 1 cm and one opening was used to mimic the dimensions of the nasal cavity. The test tube was charged with 4.00 g of water followed by 1.00 g of gel, the water and the gel in tube being separated by a small amount of air. The gel was applied in such a way that the opening of the test tube was completely sealed with gel and that the gel levelled with the opening of the test tube (no protrusion of gel from the opening). After its sealing with gel, the test tube was turned 180°, i.e. with the opening downwards. The test tube was inspected regularly for signs of leakage through the gel during 1 hour. When there were no signs of leakage at that time, the tubes were shaken by slowly lifting them 10-15 cm with the opening still oriented downwards, followed by one quick movement to bring the tube back in the original position. The time or the amount of shakes (when the seal survived the initial hour) required for the seal to break were recorded.

Dynamic Viscosity Test Method

The dynamic viscosity of the prepared gels was analyzed using a Discovery Hybrid Rheometer (HR-2) from TA Instruments. A parallel plate system was used, wherein both plates are made of stainless steel with the top (rotating) plate having a diameter of 40 mm. Measurements were performed with a gap height of 500 µm in between the plates with a controlled temperature of 32° C.

Roughly 1 mL of gel was placed on the lower plate. The top plate was first lowered to a trim height wherein excess gel that was expelled was removed. The top plate was then lowered to the measurement height and the gel was left to rest for 3 minutes. After this resting period, the measurement was started whereby the shear rate was increased from 5 to 250 1/s over the course of 4 minutes. All dynamic viscosity data were obtained at a shear rate of 10 1/s.

Results of the Tests

The water absorption, the occlusion and the dynamic viscosity were measured for the reference gel (Example 2) and the gels of the invention (Examples 3-5). The results are displayed in Table 1.

TABLE 1

Water absorption, occlusion and dynamic viscosity of the gels.

| Gel | Water absorption (%) | Occlusion | Dynamic viscosity (Pa · s) |
|---|---|---|---|
| Example 2: Reference | 29 | 45 minutes | 19.4 |
| Example 3: CMC | 99 | 1 hour, 3 shakes | 21.1 |
| Example 4: Chitosan | 117 | 1 hour, 5 shakes | 21.8 |
| Example 5: Guar | 39 | 1 hour, >15 shakes | 29.0 |

CONCLUSIONS

In the above experiments, gels of the invention were compared to a reference gel. All the gels comprise gelatin particles comprising chemical cross-links and dehydrothermal cross-links, but the reference gel differs in that it does not comprise a dissolved gelatin comprising chemical cross-links and at least one polysaccharide.

The experiments demonstrate that gels of the invention all have an improved water absorption, provide a better occlusion and have a higher dynamic viscosity than the reference gel.

The improved water absorption indicates that the gel is more effective in the treatment of haemostasis at a wound or bleeding site, since it can absorb more blood. Further, when applied in a body cavity (e.g. to treat epistaxis), the gel provides a better (i.e. stronger and longer lasting) sealing of the bleeding site.

The invention claimed is:

1. A gel comprising a first gelatin component and a second gelatin component in an aqueous medium, wherein
    the first gelatin component comprises gelatin particles comprising chemical cross-links and dehydrothermal cross-links; and
    the second gelatin component comprises a dissolved gelatin comprising chemical cross-links and at least one polysaccharide.

2. The gel according to claim 1, wherein the gelatin is derived from an animal species selected from the group consisting of pigs, cows and horses.

3. The gel according to claim 1, wherein the chemical cross-links of the gelatin particles of the first gelatin component and/or the dissolved gelatin of the second gelatin component are derived from an aldehyde.

4. The gel-according to claim 3, wherein the aldehyde is selected from the group consisting of formaldehyde, paraformaldehyde, acetaldehyde, propionaldehyde, PEG-propionaldehyde, butyraldehyde, isobutyraldehyde, valeraldehyde, heptaldehyde, decanal, terephthaldehyde, crotonaldehyde, glutaraldehyde, glyoxal, PEG-dialdehyde, dialdehyde carboxymethyl cellulose and dialdehyde starch.

5. The gel according to claim 1, wherein the at least one polysaccharide is selected from the group consisting of xanthan, dextran, gellan, levan, curdlan, cellulose, cellulose derivatives, carboxymethylcellulose, hemicellulose, pullulan, starch, cellulose, agar, agarose, alginate, carrageenan, pectin, konjac, beta-mannan gum, carob gum, fenugreek gum, guar gum, tara gum, karaya gum, tragacanth gum, arabinoxylan gum, gellan gum, xanthan gum, agar-agar, chitosan, chitosan derivatives, hyaluronic acid and hyaluronic acid derivatives.

6. The gel according to claim 1, wherein the gel comprises a buffer solution having a pH in the range of 6.8-7.4.

7. The gel-according to claim 1, wherein the particles of the first gelatin component have at least one dimension in the range of 50-750 µm.

8. A syringe which includes an effective amount of the gel according to claim 1 in order to stop bleeding at a bleeding site of a human or animal subject.

9. A method for preparing the gel according to claim 1, comprising
    (a) preparing a first gelatin component by performing the sequential steps of:
        (a1) providing an aqueous composition comprising dissolved gelatin;
        (a2) cross-linking the gelatin in the aqueous composition by treating the gelatin with a chemical cross-linking agent;
        (a3) foaming the aqueous composition to yield a foam;
        (a4) lyophilizing the foam to yield a porous solid;
        (a5) pulverizing the porous solid to yield a powder;
        (a6) exposing the powder to dehydrothermal curing; and then
        (a7) remoisturizing the powder to yield the first gelatin component;
    (b) preparing a second gelatin component by performing the sequential steps of:
        (b1) providing an aqueous composition comprising dissolved gelatin;
        (b2) cross-linking the gelatin in the aqueous composition by treating the gelatin with a chemical cross-linking agent; and then
        (b3) adding a polysaccharide to the composition; and
    (c) mixing the first gelatin component with the second gelatin component to yield the gel.

10. The method according to claim 9, wherein the chemical cross-linking agent is an aldehyde selected from the group consisting of formaldehyde, paraformaldehyde, acetaldehyde, propionaldehyde, PEG-propionaldehyde, butyraldehyde, isobutyraldehyde, valeraldehyde, heptaldehyde, decanal, terephthaldehyde, crotonaldehyde, glutaraldehyde, glyoxal, PEG-dialdehyde, dialdehyde carboxymethyl cellulose and dialdehyde starch.

11. The method according to claim 9, which comprises sieving a of cross-linked gelatin over a plurality of sieves to yield powder particles having at least one dimension that is in the range of 50-750 µm.

12. The method according to claim 9, wherein the method further comprises a step of (d) exposing the gel to a temperature in the range of 80-140° C.

13. A method of treating a bleeding site of a human or an animal, wherein the method comprises administering to the bleeding site an amount of the gel according to claim 1 effective to stop bleeding at the bleeding site.

14. The method according to claim 13, wherein the bleeding site is in the nasal or sinus cavity of the human or animal.

15. The method according to claim 13, wherein the amount effective to stop bleeding is in the range of 3-15 mL.

* * * * *